United States Patent
Shyur et al.

(10) Patent No.: US 11,517,600 B2
(45) Date of Patent: Dec. 6, 2022

(54) **USE OF *CRASSOCEPHALUM RABENS* EXTRACT IN THE TREATMENT OF BREAST CANCER**

(71) Applicant: ACADEMIA SINICA, Taipei (TW)

(72) Inventors: Lie-Fen Shyur, Taipei (TW); Maria Karmella Apaya, Taipei (TW); Meng-Ting Chang, Kaohsiung (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/963,992

(22) PCT Filed: May 29, 2018

(86) PCT No.: PCT/US2018/034956
§ 371 (c)(1),
(2) Date: Jul. 22, 2020

(87) PCT Pub. No.: WO2019/147300
PCT Pub. Date: Aug. 1, 2019

(65) Prior Publication Data
US 2021/0030825 A1 Feb. 4, 2021

Related U.S. Application Data

(60) Provisional application No. 62/620,964, filed on Jan. 23, 2018.

(51) Int. Cl.
| | | |
|---|---|---|
| A61P 35/04 | (2006.01) | |
| A61K 36/28 | (2006.01) | |
| A61K 31/045 | (2006.01) | |
| A61K 31/7032 | (2006.01) | |
| A61K 31/704 | (2006.01) | |

(52) U.S. Cl.
CPC ............ *A61K 36/28* (2013.01); *A61K 31/045* (2013.01); *A61K 31/704* (2013.01); *A61K 31/7032* (2013.01); *A61P 35/04* (2018.01)

(58) Field of Classification Search
CPC ...................................................... A61P 35/04
See application file for complete search history.

(56) References Cited

U.S. PATENT DOCUMENTS

| | | | |
|---|---|---|---|
| 8,048,455 B2 | 11/2011 | Shyur et al. | |
| 2008/0152737 A1 | 6/2008 | Yi-Ping et al. | |
| 2010/0317603 A1* | 12/2010 | Shyur | A61K 36/41 514/25 |
| 2014/0350102 A1* | 11/2014 | Dalton | A61K 31/167 514/522 |

FOREIGN PATENT DOCUMENTS

| | | |
|---|---|---|
| TW | I347192 | 8/2011 |
| WO | 2015/150839 | 10/2015 |
| WO | 2015/150839 A1 | 10/2015 |
| WO | 2017/116476 A1 | 7/2017 |

OTHER PUBLICATIONS

Adewale et al., Evaluation of acute and subacute toxicity of aqueous extract of Crassocephalum rubens leaves in rats. Journal of ethnopharmacology, (Jul. 21, 2016) vol. 188, pp. 153-158 (Year: 2016).*
Hou, A galactolipid possesses novel cancer chemopreventive effects by suppressing inflammatory mediators and mouse B16 melanoma. Cancer research, (Jul. 15, 2007) vol. 67, No. 14, pp. 6907-6915 (Year: 2007).*
Jayaprakasam et al, Tumor Cell Proliferation and Cyclooxygenase Enzyme Inhibitory Compounds in Amaranthus tricolor. Journal of Agricultural and Food Chemistry (2004), 52(23), 6939-6943 (Year: 2004).*
Office Action dated Aug. 30, 2019 in ROC (Taiwan) Patent Application No. 107118226.
Search Report dated Aug. 30, 2019 in ROC (Taiwan) Patent Application No. 107118226.
English translation to Search Report dated Aug. 30, 2019 in ROC (Taiwan) Patent Application No. 107118226.
English translation to TW I347192.
Global Bio & Investment, "Establish Chinese herbal medicine industry platform to seize tens of billions of new plant medicine business opportunities" obtained on Jul. 30, 2018, http://www.gbimonthly.com/2016/11/6901/, Nov. 29, 2016 (D2); and an English translation.
Office Action dated Feb. 26, 2020 in ROC (Taiwan) Patent Application No. 107118226.
ISR for International Application PCT/US2018/034956.
Written Opinion for International Application PCT/US2018/034956.
Jung-Hyun Kim et al., "Attenuation of breast tumor cell growth by conjugated linoleic acid via inhibition of 5-lipoxygenase activating protein", Biochimica et Biophysica Acta, (20050000), vol. 1736, doi:doi:10.1016/j.bbalip.2005.08.015, pp. 244-250, XP005103842 [A] 1-17.
Maria Karmella Apaya et al., "Phytomedicine polypharmacology: Cancer therapy through modulating the tumor microenvironment and oxylipin dynamics", Pharmacology & Therapeutics, (20160000), vol. 162, doi:doi:10.1016 /j.pharmthera.2016.03.001, pp. 58-68, XP029556716 [A] 1-17.
Shao-Xing Songa, et al, "The anomeric mixture of some O-galactolipid derivatives is more toxic against cancer cells than either anomer alone", Bioorganic & Medicinal Chemistry Letters, (20120000), vol. 22, doi:doi:10.1016/j. bmcl.2012.01.069, pp. 2030-2032, XP028459451 [A] 1-17.
Office Action issued in Applicant's counterpart ROC (Taiwan) Patent Application No. 107118226.

(Continued)

*Primary Examiner* — Qiuwen Mi
(74) *Attorney, Agent, or Firm* — Ladas & Parry LLP

(57) ABSTRACT

A method for treating breast cancer and/or treating breast cancer metastasis in a subject in need of such treatment including administering to said subject an effective amount of *Crassocephalum rabens* extract and optionally a pharmaceutically acceptable carrier or excipient.

13 Claims, 14 Drawing Sheets

(56) References Cited

OTHER PUBLICATIONS

Search Report issued in Applicant's counterpart ROC (Taiwan) Patent Application No. 107118226.
Written Opinion issued on Applicant's corresponding application in Singapore dated Mar. 4, 2002, i.e., Singapore Patent Application No. 11202007005U.
Jung-Hyun Kim, et al.: Attenuation of breast tumor cell growth by conjugated linoleic acid via inhibition of 5-lipoxygenase activating protein: in Biochimica et Biophysica Acta, 2005, vol. 1736, pp. 244-250.
Maria Karmella Apaya, et al.: Phytomedicine polypharmacology: Cancer therapy through modulating the tumor microenvironment and oxylipin dynamics: in Pharmacology & Therapeutics, 2016, vol. 162, pp. 58-68.
Shao-Xing Song, et al.: The anomeric mixture of some O-galactolipid derivatives is more toxic against cancer cells than either anomer alone: in Bioorganic & Medicinal Chemistry Letters, 2012, vol. 22, pp. 2030-2032.

\* cited by examiner

USE OF *CRASSOCEPHALUM RABENS* EXTRACT IN THE TREATMENT OF BREAST CANCER

BACKGROUND

1. Field of the Disclosure

The present disclosure relates to use of *Crassocephalum rabens* extract, and more particularly to use of *Crassocephalum rabens* extract in the treatment of breast cancer.

2. Description of the Related Art

Triple negative breast cancer (TNBC) is an aggressive breast cancer subtype characterized by the absence/low expression of targetable estrogen (ER), progesterone (PR), and human epidermal growth factor (HER2) receptors (Sledge G W, Mamounas E P, Hortobagyi G N, et al. (2014) Past, present, and future challenges in breast cancer treatment. J Clin Oncol 32 (19):1979-1986). After surgery, only cytotoxic chemotherapy works for preventing tumor growth and metastasis in tumor patients (Zeichner S B, Terawaki H and Gogineni K (2016) A review of systemic treatment in metastatic triple negative breast cancer. Breast Cancer (Auckl) 10:25-36). One of the most commonly administered chemotherapy drug for TNBC in the market today is doxorubicin (Adriamycin®; formulated as doxorubicin hydrochloride) (Piccart-Gebhart M J, Burzykowski T, Buyse M, et al. (2008) Taxanes alone or in combination with anthracyclines as first-line therapy of patients with metastatic breast cancer. J Clin Oncol. 26:1980-1986). It is clinically used in combination with other taxanes or anthracyclines such as docetaxel and cyclophosphamide, respectively (Wahba H A and El-Hadaad H A. (2016) Current approaches in treatment of triple-negative breast cancer. Cancer Biol Med 12 (2): 106-116). The limited efficacy and unwarranted side effects of these combination treatments, however, prompt efforts to be directed towards the discovery of novel and targetable TNBC-specific mechanisms. For instance, it has been shown that most current chemotherapeutic regimens primarily act via inducing apoptotic tumor responses in TNBC tumors (O'Reilly E A, Gubbins L, Sharma S, et al. (2015) The fate of chemoresistance in triple negative breast cancer (TNBC). BBA Clinical 3:257-275). Cancer cells, however, maintain viability via chemoresistance or metastasis. Aside from higher rates of metastatic relapse in TNBC patients, these cancer cell survival mechanisms against current therapeutic strategies make optimization of effective chemotherapy combinations challenging (Collignon J, Lousberg L, Schroeder H, and Jerusalem G (2016). Triple-negative breast cancer: treatment challenges and solutions. Breast Cancer: Target & Ther 8, 93-107). Moreover, side effects including weight loss, compromised immune response, cachexia, and fatigue are commonly associated with these schemes (Hanna A D, Lam A, Tham S, Dulhunty A F, and Beard N A. (2014) Adverse effects of doxorubicin and its metabolic product on cardiac RyR2 and SERCA2A. Mol Pharmacol 86 (4):438-449). Doxorubicin treatment is also well-known to induce cardiomyopathy, one of the more serious and lethal chemotherapeutic side effects for TNBC patients (Chatterjee K, Zhang J, Honbo N and Karliner J S. (2010) Doxorubicin cardiomyopathy. Cardiology 115 (2):155-162). Because of these reasons, more effective compounds showing less cytotoxic effects on normal cells, but has higher efficacy against cancer cells are desired (Craig D W, O'Shaughnessy J A, Kiefer J A, et al. (2013) Genome and transcriptome sequencing in prospective metastatic triple-negative breast cancer uncovers therapeutic vulnerabilities. Mol Cancer Ther 12 (1):104-116).

SUMMARY

The present disclosure provides use of *Crassocephalum rabens* extract in the treatment of breast cancer.

The present disclosure provides a method for treating breast cancer and/or treating breast cancer metastasis in a subject in need of such treatment comprising administering to said subject an effective amount of *Crassocephalum rabens* extract and optionally a pharmaceutically acceptable carrier or excipient.

The present disclosure provides use of *Crassocephalum rabens* extract in the manufacture of a medicament for treating breast cancer and/or treating breast cancer metastasis.

The present disclosure provides a pharmaceutical composition for treating breast cancer and/or treating breast cancer metastasis comprising an effective amount of *Crassocephalum rabens* extract and optionally a pharmaceutically acceptable carrier or excipient.

The present disclosure provides *Crassocephalum rabens* extract for use in treating breast cancer and/or treating breast cancer metastasis.

The present disclosure provides a method for treating breast cancer and/or treating breast cancer metastasis in a subject in need of such treatment comprising administering to said subject an effective amount of a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof and optionally a pharmaceutically acceptable carrier or excipient;

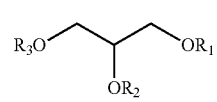

Formula I wherein of $R_1$ and $R_2$, independently, is $C(O)R_a$ in which $R_a$ is $C_{15-17}$ alkyl having 0 to 3 double bonds, and $R_3$ is monogalactosyl or digalactosyl.

The present disclosure provides use of a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof in the manufacture of a medicament for treating breast cancer and/or treating breast cancer metastasis.

The present disclosure provides a pharmaceutical composition for treating breast cancer and/or treating breast cancer metastasis comprising an effective amount of a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof and optionally a pharmaceutically acceptable carrier or excipient.

The present disclosure provides a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof for use in treating breast cancer and/or treating breast cancer metastasis.

The present invention is described in detail in the following sections. Other characteristics, purposes and advantages of the present invention can be found in the detailed description and claims.

BRIEF DESCRIPTION OF THE DRAWINGS

FIG. 4A are survival curves showing that groups treated with CR-API and dLGG had lower rates of mortality compared with the tumor control and Dox-treated groups. FIG. 4B shows that Dox-induced weight loss was attenuated by combination treatment with dLGG5. No significant weight loss was observed for groups treated with either CR-API or dLGG only. Data are mean±SEM, N=8.

FIG. 5A shows that tumor volumes for all treatment groups were measured every 3 days after implantation. At the end of the observation period (30 days), significant tumor volume reduction was observed for the Dox5 (P<0.0001), Dox5+dLGG5 (P=0.0015) and dLGG25 (P=0.0015) treated mice compared with the tumor control. FIG. 5B shows that at day 30, tumors were harvested and their weights were recorded. Tumor weights for Dox5, Dox5+dLGG5, CR-API400, dLGG5 and dLGG25 treatment groups were significantly lower compared with the tumor control group. FIG. 5C shows representative tumors for all the different treatment groups. Reduction of tumor weights are calculated as % compared with the tumor control (scale bar, 5 mm).

FIG. 7A shows representative H&E images of lung tissues for all the treatment groups. The images show that metastatic tumor nodules were visible in the tumor control group, dLGG5 and CR-API200 groups but were not detectable in dLGG25, CR-API400, Dox5 and Dox5+dLGG5 groups. FIG. 7B represents IHC analysis showing high Ki67-expressing metastatic TNBC nodules in the lungs of test animals (scale bar, 50 µm).

DETAILED DESCRIPTION

Figure 1:
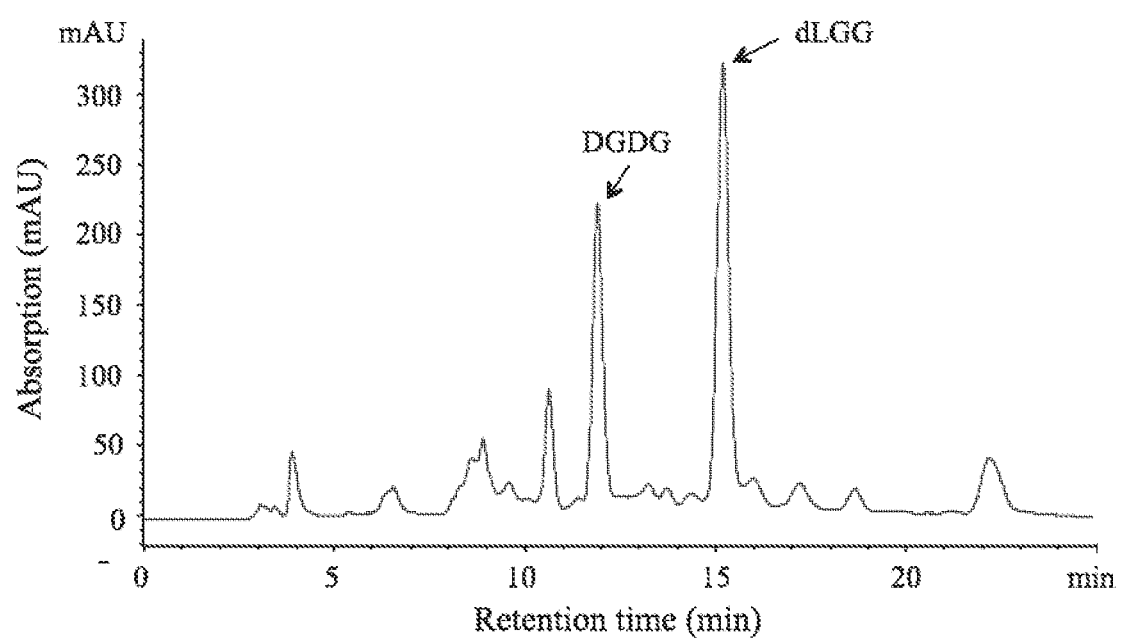
FIG. 1 shows HPLC profile of CR-API extract from *C. rabens* determined at absorbance 210 nm. The retention time (Rt) of the bioactive compounds 1,2-di-O-α-linolenoyl-3-O-(6-O-α-galactopyranosyl-β-galactopyranosyl)-sn-glycerol (DGDG) and 1,2-di-O-α-linolenoyl-3-O-β-galactopyranosyl-sn-glycerol (dLGG) were detected around 12 and 15 min, respectively.

The present disclosure provides a method for treating breast cancer and/or treating breast cancer metastasis in a subject in need of such treatment comprising administering to said subject an effective amount of *Crassocephalum rabens* extract and optionally a pharmaceutically acceptable carrier or excipient.

The present disclosure provides use of *Crassocephalum rabens* extract in the manufacture of a medicament for treating breast cancer and/or treating breast cancer metastasis.

The present disclosure provides a pharmaceutical composition for treating breast cancer and/or treating breast cancer metastasis comprising an effective amount of *Crasso-

*cephalum rabens* extract and optionally a pharmaceutically acceptable carrier or excipient.

The present disclosure provides *Crassocephalum rabens* extract for use in treating breast cancer and/or treating breast cancer metastasis.

The present disclosure provides a method for treating breast cancer and/or treating breast cancer metastasis in a subject in need of such treatment comprising administering to said subject an effective amount of a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof and optionally a pharmaceutically acceptable carrier or excipient;

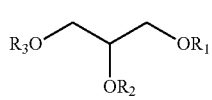

Formula I wherein of $R_1$ and $R_2$, independently, is $C(O)R_a$ in which $R_a$ is $C_{15-17}$ alkyl having 0 to 3 double bonds, and $R_3$ is monogalactosyl or digalactosyl.

The present disclosure provides use of a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof in the manufacture of a medicament for treating breast cancer and/or treating breast cancer metastasis.

The present disclosure provides a pharmaceutical composition for for treating breast cancer and/or treating breast cancer metastasis comprising an effective amount of a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof and optionally a pharmaceutically acceptable carrier or excipient.

The present disclosure provides a compound represented by Formula I, 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG), or a pharmaceutically acceptable derivative thereof for use in treating breast cancer and/or treating breast cancer metastasis.

The present invention can be more readily understood by reference to the following detailed description of various embodiments of the disclosure, the examples, and the chemical drawings and tables with their relevant descriptions. It is to be understood that unless otherwise specifically indicated by the claims, the invention is not limited to specific preparation methods, carriers or formulations, or to particular modes of formulating the extract of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

The term "a pharmaceutically acceptable derivative" or "pharmaceutically acceptable derivatives" as used herein denotes a compound that is modified from the compound of the disclosure but has properties and efficacies that are the same as or better than those of the compound of the disclosure. Preferably, the pharmaceutically acceptable derivative is a pharmaceutically acceptable salt, solvate, hydrate, or prodrug of the compound of the disclosure.

The compounds of the disclosure can also exist as solvates and hydrates. Thus, these compounds may crystallize with, for example, waters of hydration, or one, a number of, or any fraction of molecules of the mother liquor solvent. The solvates and hydrates of such compounds are included within the scope of this invention.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Phytocompounds modulating key processes in cancer and immune cell metabolism are rich resources towards developing more effective chemotherapeutic agents. They may be used alone or in combination with currently available drugs to enhance their effectiveness or minimize their side effects.

The *Crassocephalum rabens* according to the invention is also known as *C. rabens* S. Moore, *C. rubens* S. Moore, *C. crepidioides* S. Moore, and *Crassocephalum crepidioides*. As used herein, *Crassocephalum rabens* plant may be the whole plant or one or more parts thereof, including but not limited to, seeds, flowers, leaves, stems and roots. In an embodiment of the present invention, the *Crassocephalum rabens* plant is the whole plant. In another embodiment of the present invention, the *Crassocephalum rabens* plant is seeds, flowers, leaves, or any combination thereof. In a preferred embodiment of the present invention, the *Crassocephalum rabens* plant is dried and powdered.

The *Crassocephalum rabens* extract according to the invention is preferably an alcohol extract. Preferably, the alcohol is C1 to C4 alcohol. The term "C1 to C4 alcohol" as used herein refers to linear or branched, substituted or unsubstituted, mono- or poly-functional, and saturated or unsaturated alcohol; preferably unsubstituted, mono-functional and saturated alcohol. In one preferred embodiment of the disclosure, the C1 to C4 alcohol is selected from the group consisting of methanol, ethanol, n-propanol, isopropanol, n-butanol, iso-butanol, sec-butanol, tert-butanol. More preferably, the C1 to C4 alcohol is methanol or ethanol. The C1 to C4 alcohol can be used solely or in combinations.

In one preferred embodiment of the disclosure, the *Crassocephalum rabens* extract is an ethyl acetate sub-fraction of the alcohol extract. In one more preferred embodiment of the disclosure, a further purification such as high performance liquid chromatography is utilized for the isolation of active compounds from the alcohol extract or the ethyl acetate sub-fraction thereof.

In one preferred embodiment of the disclosure, the *Crassocephalum rabens* extract is prepared by a process including mixing a *C. rabens* plant with alcohol to form a first solution; removing alcohol from the first solution to obtain a second solution; adding ethyl acetate to the second solution to form an organic portion and an inorganic portion (or, water portion); separating the organic portion into a multiple fractions; and collecting a fraction containing a galactolipid compound. For example, the organic portion can be separated on a silica gel column with a solution containing dichloromethane and methanol to obtain the fraction containing a galactolipid compound.

The galactolipid compound contained in the *Crassocephalum rabens* extract according to the invention includes but is not limited to 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1,2-di-O-α-linolenoyl-3-O-(6-O-α-galactopyranosyl-β-galactopyranosyl)-sn-glycerol (DGDG).

The extract can include a galactolipid compound of Formula I:

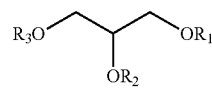

Formula I wherein of $R_1$ and $R_2$, independently, is $C(O)R_a$ in which $R_a$ is $C_{15-17}$ alkyl having 0 to 3 double bonds, and $R_3$ is monogalactosyl or digalactosyl. In one embodiment, the monogalactosyldiacylglycerol is selected from the group consisting of 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1) and 1,2-di-O-α-linolenoyl-3-O-(6-O-α-galactopyranosyl-β-galactopyranosyl)-sn-glycerol (DGDG). Preferably, the compound is dLGG.

The compounds of the disclosure can be further converted into a pharmaceutically acceptable derivative, such as a pharmaceutically acceptable salt, solvate or prodrug, by any known methods.

The *Crassocephalum rabens* extract is preferably contained in an extraction composition.

The extraction composition according to the invention is preferably a pharmaceutical composition, food composition or a cosmetic composition.

The pharmaceutical composition according to the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The external route as used herein is also known as local administration, includes but is not limited to administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol.

Topical preparations may be administered by one or more applications per day to the affected area; over the skin areas occlusive dressings may advantageously be used. Continuous or prolonged delivery may be achieved by an adhesive reservoir system.

The cosmetic composition according to the invention may be an aqueous phase formulation consisting essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, C3-C4 ketones and C2-C4 aldehydes, and glycerin. Such an aqueous formulation preferably is in a form of aqueous gel or hydrogel formulation. The hydrogel formulation comprises a thickening agent to thicken the liquid solution. Examples of the thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition are preferably used.

The cosmetic composition according to the present invention may be in a form of emulsion or cream formulation. It can contain emulsifying surfactants. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants.

The surfactants preferably used in the cosmetic composition according to the invention are chosen from: nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of C1-C6 alkyl glucose, and mixtures thereof; anionic surfactants: C16-C30 fatty acids neutralized with amines, aqueous ammonia or alkaline salts, and mixtures thereof. Surfactants which make it possible to obtain an oil-in-water or wax-in-water emulsion are preferably used.

The cosmetic composition according to the invention may further comprise an effective amount of a physiologically acceptable antioxidant selected from the group consisting of butylated p-cresol, butylated hydroquinone monomethyl ether, and a tocopherol.

The cosmetic composition according to the invention may further comprise natural or modified amino acid, natural or modified sterol compound, natural or modified collagen, silk protein or soy protein.

The cosmetic composition according to the invention is preferably formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The cosmetic composition according to the invention may be more or less fluid and may have the appearance of a white or colored cream, an ointment, a milk, a lotion, a serum, a paste, a mousse or a gel. It may optionally be topically applied onto the skin in the form of an aerosol, a patch or a powder. It may also be in solid form, for example, in the form of a stick. It may be used as care products and/or as makeup products for the skin. Alternatively, it may be formulated as shampoos or conditioners.

In known fashion, the cosmetic composition according to the invention may also contain additives and adjuvants that are common in cosmetics, such as hydrophilic or lipophilic gelling agents, preservatives, antioxidants, solvents, fragrances, fillers, pigments, odor absorbers and dyestuffs.

The extract composition can be added to a conventional food composition (i.e. the edible food or drink or precursors thereof) in the manufacturing process of the food composition. Almost all food compositions can be supplemented with the extract composition of the disclosure. The food compositions that can be supplemented with the extract composition of the disclosure include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

As used herein, the term "metastasis" refers to a cancer spreads from an initial or primary site to a different or secondary site within a subject. The spread of cancer cells from the place where they first formed to another part of the body. In metastasis, cancer cells break away from the original (primary) tumor, travel through the blood or lymph system, and form a new tumor in other organs or tissues of the body. Preferably, the *Crassocephalum rabens* extract or galactolipid compounds contained in the *Crassocephalum rabens* extract is effective in treating breast cancer metastasis to the lung or liver. In one embodiment of the disclosure, expression levels of a proliferation marker in metastasis sites (lungs and liver) are attenuated by the treatment with either *Crassocephalum rabens* extract or pure galactolipid compound in a dose dependent manner. In another embodiment of the disclosure, tumor metastasis-induced inflammation in liver and lung tissues were also decreased by the treatment with either *Crassocephalum rabens* extract or pure galactolipid compound.

Preferably, the *Crassocephalum rabens* extract or galactolipid compounds contained in the *Crassocephalum rabens* extract is effective in decreasing expression levels of metastasis related proteins selected from the group consisting of Src, FAK, Rac 1, Cav-1, CYP2C19 and COX-2. In one embodiment of the disclosure, western blotting results show that the treatment with either *Crassocephalum rabens* extract or pure galactolipid compound decreases expression levels of metastasis related proteins important in tumor microenvironment sensing (Src and FAK), membrane remodeling (Rac1 and Cav-1), and bioactive lipid metabolism (CYP2C19 and COX-2).

The breast cancer according to the present disclosure is a cancer that develops from breast tissue. The breast cancer comprises breast cancer cells. Examples of the breast cancer cells include but are not limited to ER+ breast cancer cells, Her2+ breast cancer cells and ER−, PR− and Her2− breast cancer cells.

Preferably, the *Crassocephalum rabens* extract or galactolipid compounds contained in the *Crassocephalum rabens* extract is effective in inhibiting breast cancer cell proliferation. In one embodiment of the disclosure, the treatment with either *Crassocephalum rabens* extract or pure galactolipid compound significantly reduces tumor masses compared with the tumor control group. Furthermore, in one embodiment of the disclosure, expression levels of a proliferation marker in tumor tissues are attenuated by the treatment with either *Crassocephalum rabens* extract or pure galactolipid compound in a dose dependent manner.

Preferably, the *Crassocephalum rabens* extract or galactolipid compounds contained in the *Crassocephalum rabens* extract is effective in promoting apoptosis of breast cancer cells. In one embodiment of the disclosure, expression of an apoptosis marker in tumor tissues is increased in by the treatment with either *Crassocephalum rabens* extract or pure galactolipid compound compared with the tumor control.

Preferably, the *Crassocephalum rabens* extract or galactolipid compounds contained in the *Crassocephalum rabens* extract is effective in suppressing tumor induced inflammation or metastasis-induced inflammation.

Preferably, the *Crassocephalum rabens* extract or galactolipid compounds contained in the *Crassocephalum rabens* extract is effective in increasing survival rate of the subject. In one embodiment of the disclosure, treatment with either *Crassocephalum rabens* extract or pure galactolipid compound increases the survival rate of tumor-inoculated animals compared with the groups treated with the anti-cancer drug, doxorubicin (Dox) and the tumor (vehicle-treated) control group.

In one preferred embodiment of the disclosure, the treatment is combined with other anti-cancer agents. Examples of the anti-cancer agents according to the invention include but are not limited to doxorubicin, taxanes or anthracyclines, such as docetaxel and cyclophosphamide, epirubicin, bevacizumab, gemcitabine, 5-fluorouracil, capecitabine, cyclophosphamide, carboplatin, cisplatin, oxaliplatin, or vinblastine; preferably, doxorubicin.

Preferably, the *Crassocephalum rabens* extract or galactolipid compounds contained in the *Crassocephalum rabens* extract is effective in attenuating the side effects of the anti-cancer agents. Examples of the side effects include but are not limited to body weight loss, compromised immune response, cachexia, fatigue, cardiomyopathy, and COX-2 overexpression. In some embodiment of the disclosure, Dox-induced body weight loss was attenuated by combination treatment with low-dose galactolipid compounds, while no significant weight loss was observed for groups treated with either *Crassocephalum rabens* extract or galactolipid compounds only. Moreover, COX-2 overexpression induced by the anti-cancer agents-treatment in distal organs is attenuated by Dox and galactolipid compounds combination treatment.

The following Examples are given for the purpose of illustration only and are not intended to limit the scope of the present invention.

*Crassocephalum rabens* Extraction

Fresh whole *Crassocephalum rabens* S. Moore (Asteraceae) (also known as *C. crepidioides* S. Moore) plants were extracted with 70% ethanol for one week and repeated twice. The crude extract was further fractionated using Biotage-Flash Purification system with a SNAP cartridge, KP-C18-HS, and eluted with aqueous ethanol (76%-100%, w/w). The cartridge volumes (cv) between cv9 to cv12 were collected to yield the CR-API extracts. The metabolite profile of CR-API was performed on a Phenomenex Luna C18(2) column (5 µm, 250×4.6 mm) in Agilent 1100 Series HPLC system with a diode array detector (UV/DAD). The elution condition was using a mobile phase with isocratic 98% methanol elution at a flow rate of 1 mL/min. The wavelength was setting in the range 190-400 nm and representative chromatogram was acquired at 210 nm. A representative column chromatogram of CR-API is shown in FIG. 1, in which the index and bioactive compound dLGG appeared around 15 min.

Isolation of dLGG

CR-API extracts were further purified using preparative RP-HPLC (Cosmosil, 5C18-AR-II column, 250×20 mm) to collect pure dLGG. The retention time of dLGG appeared around 37 min (98% methanol, 5 mL/min, A210 nm), and the purity and structure of dLGG (>98%) was examined by analytical RP-HPLC (Phenomenex Luna 5 μm C18(2) column, 250×4.6 mm) and NMR spectrometry by Bruker AVII 500 NMR (data not shown).

EXAMPLE

*Crassocephalum rabens* Extract and Galactolipid Compound for Treating Breast Cancer and/or Treating Breast Cancer Metastasis

Materials and Methods

Reagents and Antibodies 3-(4,5-Dimethylthiazol-2-yl)-2,5-diphenyltetrazolium bromide (MTT) and dimethyl sulfoxide (DMSO) were purchased from Sigma-Aldrich. Molecular weight markers for SDS-PAGE were estimated by using prestained protein markers (Bioman, Taipei, Taiwan). Primary antibodies against actin (Millipore), Ki-67, cleaved caspase-3, Src, phospho-(419 and 547) Src (abcam), CAV-1 (Thermoscientific) and COX-2, FAK, phospho-FAK, CYP2C19, Rac1 (Santa Cruz) were used. All other chemicals and solvents were of reagent or high performance liquid chromatography (HPLC) grade.

Cell Lines and Culture Conditions

Immortalized normal human mammary epithelial cells (MCF10A) and breast cancer cell lines including HER2+ (SKBR3), ER+ (MCF7), triple negative (MDA-MB-231), and murine TNBC cell line 4T1 were obtained from the ATCC (USA). Cells were expanded and frozen at low passage after the receipt of the original stocks. Cells were thawed and used within 15 passages. Cells were cultured in manufacturers' suggested medium supplemented with 10% FBS, 100 units/mL penicillin, and 100 mg/mL streptomycin at 37° C. humidified 5% $CO_2$ incubator.

Animals

Female BALB/cByJNarl mice (4-week-old) were supplied from National Laboratory Animal Center, Taipei, Taiwan and given a standard laboratory diet and distilled water ad libitum and kept on a 12-h light/dark cycle at 22±2° C. This study was conducted according to the institutional guidelines and approved by the Institutional Animal Care and Utilization Committee (IACUC) of Academia Sinica, Taiwan.

Cell Viability Assay

Cells ($3 \times 10^3$ cells/well) were seeded in 96-well plates overnight and treated for 24 hours. Cell growth was determined by MTT-based colorimetric assay. Viability of the cells treated with vehicle-only (0.5% DMSO) was defined as 100% viability. Cell survival after compound treatment was calculated using the following formula: viable cell number (%)=[$OD_{570}$ (treated cells)/$OD_{570}$ (vehicle control)]×100.

In Vivo Effects of CR-API and dLGG Against TNBC

Figure 2:
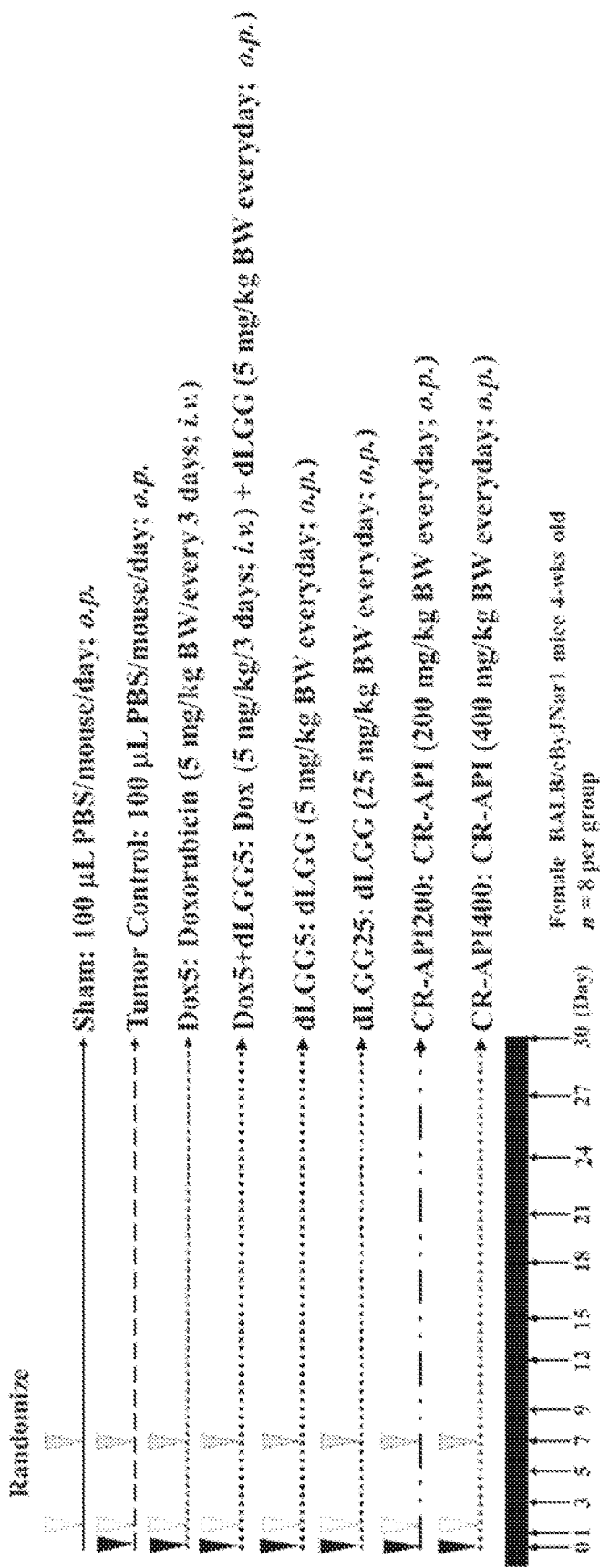
FIG. 2 shows experimental design and treatment scheme for the 4T1 orthotopic breast cancer model used to evaluate the effects of dLGG and dLGG-enriched fraction (CR-API) derived from *C. rabens*. Doxorubicin was used as positive control. Drug and compound/extract effects on tumor size were monitored every 3 days. All test animals were euthanized at day 30.

The therapeutic effects of dLGG or dLGG-enriched CR-API fractions from *C. rabens* against TNBC were evaluated using an orthotopic tumor model. Briefly, mice were subcutaneously injected with 4T1 (murine TNBC) cells ($5 \times 10^6$ cells per 100 μl PBS and 50 μl matrigel per mouse) into the fourth mammary fat pad under isoflurane anaesthesia. Tumor growth and body weight are monitored daily. After tumors grow to an approximate size of 150 $mm^3$ at day 7 post implantation, test mice are randomized into different groups (8 mice per group) and subjected to a three-week compound treatment scheme (FIG. 2). Test mice are grouped accordingly: sham control (PBS o.p.); tumor control (PBS o.p.); doxorubicin administered at 5 mg/kg every 3 days i.v. (Dox5); low and high dose dLGG treatment, 5 and 25 mg/kg daily o.p., respectively (dLGG5 and dLGG25); doxorubicin and low dose dLGG combination treatment (Dox5+dLGG5); and low and high dose CR-API treatment at 200 and 400 mg/kg daily o.p., respectively (CR-API200 and CR-API400). Dosage and frequency of doxorubicin treatment is based on maximum tolerable dose determined from in house toxicity experiments within the concentration range commonly used in animal studies (Bao L, Haque A, Jackson K, et al. (2011) Increased Expression of P-Glycoprotein Is Associated with Doxorubicin Chemoresistance in the Metastatic 4T1 Breast Cancer Model. The American Journal of Pathology. 2011; 178 (2):838-852). Effects of drug/compound/extracts are evaluated thrice a week by monitoring tumor size and body weight. Euthanasia by cervical dislocation are performed at day 30 post tumor implantation. Tumors, organ tissues (lungs, liver, kidneys, spleen) and serum were immediately collected and allocated either for western blotting (immediately flash frozen using $N_2$ and stored at −80° C.) or for paraffin fixation (immediately soaked in 10% formalin solution for at least one week). Paraffin-embedded tissues were stored at room temperature. Detailed experimental design for this animal study is shown in FIG. 2.

Histology and Immunohistochemistry

Tumor and organ tissues were fixed in 10% buffered formalin and embedded in paraffin. Paraffin-embedded samples were sectioned (6 μm) and underwent hemotoxylin and eosin (H&E) or immunohistochemical (IHC) staining. Paraffin-embedded tissue sections were heat immobilized and deparaffinized using xylene and rehydrated in a graded series of ethanol with a final wash in distilled water. For antigen retrieval, citrate retrieval buffer and Decloaking Chamber (Biocare Medical) were used. Images were captured using AxioVision software (Carl Zeiss MicroImaging, Inc.).

Western Blotting

Total protein of tumor tissues (0.1 g) from each mouse was homogenized in a mixer ball mill (MM301, Retsch, Haan, Germany) for 2 min, extracted by adding 0.4 mL RIPA lysis buffer and centrifuged at 15,000×g for 30 min at 4° C. The supernatant was collected, and total protein concentrations of samples were determined by use of a DC protein assay kit (Bio-Rad). Protein was resolved by 10% gradient SDS-PAGE and immunoblotted with enhanced chemiluminescence reagents (ECL, Amersham) and antibodies against specified protein.

Data Analysis

Quantification for all data derived from the animal experiments are expressed as mean±SEM. 3-5 mice representative of all treatment groups were presented in cases where all cannot be presented simultaneously.

Results and Discussion dLGG Inhibits Various Breast Cancer Cell Proliferation

Figure 3:
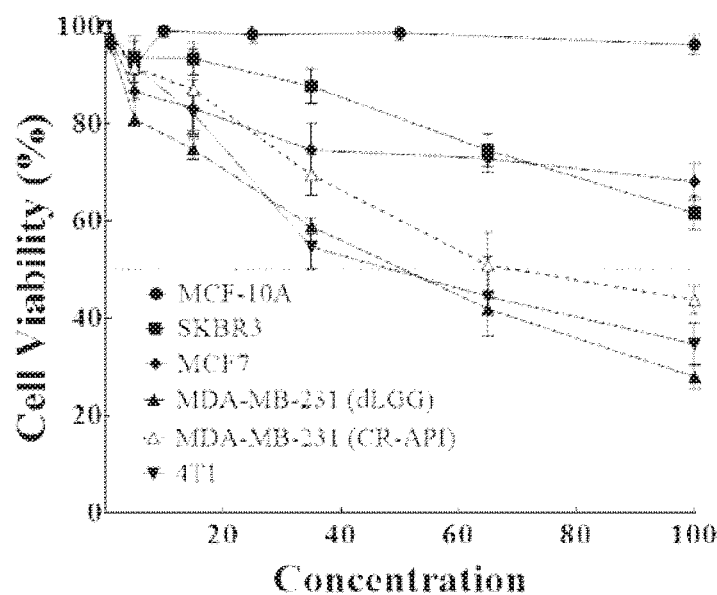
FIG. 3 shows that dLGG-treatment significantly reduced in vitro viability of TNBC cells. Cells ($3\times10^3$ cells/well) were treated with indicated concentrations of dLGG (µM) or CR-API (µg/mL) for 24 hours. Cell viability was determined using MTT assay. Data presented are representative of 3 independent experiments, with 5 technical replicates each.

We first evaluated the anti-proliferative effects of CR-API or dLGG using human derived MCF10A (normal mammary epithelial cells), MCF7 (ER+ breast cancer cells), SKBR3 (Her2+ breast cancer cells), MDA-MB-231 (ER−, PR− and Her2− TNBC cells) and murine derived 4T1 TNBC cells (FIG. 3). $IC_{50}$ for CR-API was reached at 65 μg/mL in MDA-MB-231 cell line. For both human and murine derived TNBC cells, $IC_{50}$ was at 55 μM for dLGG, while $IC_{50}$ was not reached for the other human-derived breast cancer cells at the tested concentration range (5-100 μM). Interestingly, no significant change in cell survival following 24 h dLGG treatment was observed for MCF10A. These results highlight the efficacy of CR-API and dLGG in inhibiting TNBC cell proliferation without showing toxic effects on normal mammary epithelial cells.

Figure 4A:
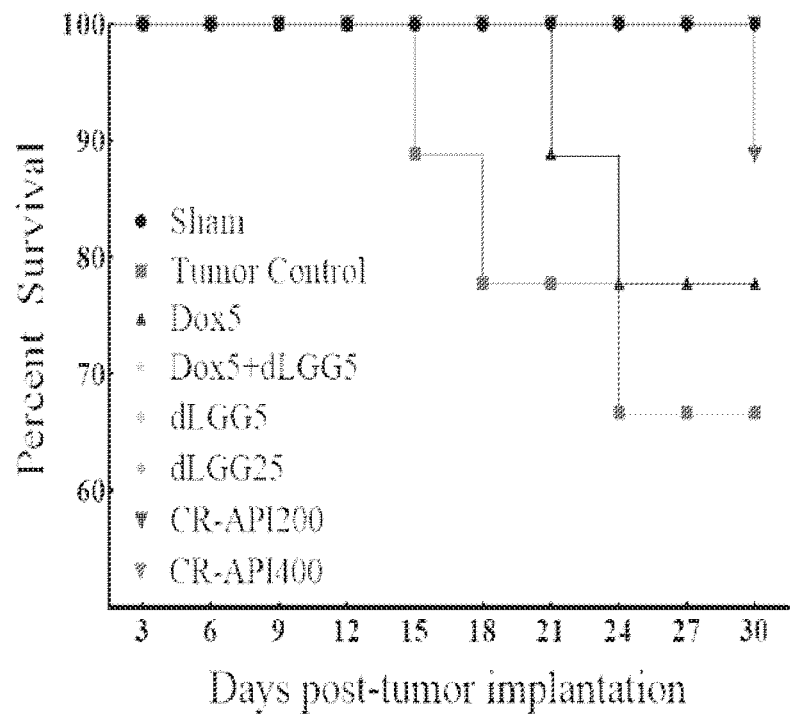
FIGS. 4A to 4B show that CR-API and dLGG treatment prolong survival and sustained normal body weight in tumor-implanted animals. Tumor-bearing mice were treated with PBS (tumor control), Dox5 (5 mg/kg every 3 days; iv.), dLGG5 (5 mg/kg daily; o.p.), dLGG25 (25 mg/kg daily; o.p.), CR-API200 (200 mg/kg daily; o.p.), CR-API400 (400 mg/kg daily; o.p.) and Dox5+dLGG5 combination treatment.

CR-API or dLGG Treatment Shows Better Survival Rate Than Dox Treatment in TNBC Mouse Model We investigated the efficacy of dLGG-enriched CR-API fraction and the pure dLGG compound on mouse mammary 4T1 orthotopic tumor growth and metastasis in allograft mice. The commercially used chemotherapeutic drug, doxorubicin, was used as a positive control. We also performed combination treatment (Dox5+dLGG5) using dLGG and doxorubicin to assess the potential of dLGG on reducing doxorubicin-induced side effects. Oral treatment with low (dLGG5) and high (dLGG25) doses of dLGG, and low (CR-API200) and high (CR-API400) doses of CR-API, were used to assess dose dependent effects of compound/extracts on tumor-implanted animals. Our results show that at the end of the treatment period of 30 days, percentage of surviving animals was significantly higher in all CR-API and dLGG, and Dox5+dLGG5-treated groups compared with the tumor control and Dox5-treated groups (FIG. 4A). 100% survival was attained for dLGG5, dLGG25, CR-API400, and Dox5+dLGG5 treatments. These results suggest that treatment with either dLGG-enriched fraction or dLGG pure compound do not induce any unwarranted toxicity and has a positive effect on the overall welfare of the tumor-implanted mice. This also suggests that combination treatment with dLGG may alleviate doxorubicin-induced body weight loss or side effects in TNBC.

Figure 4B:
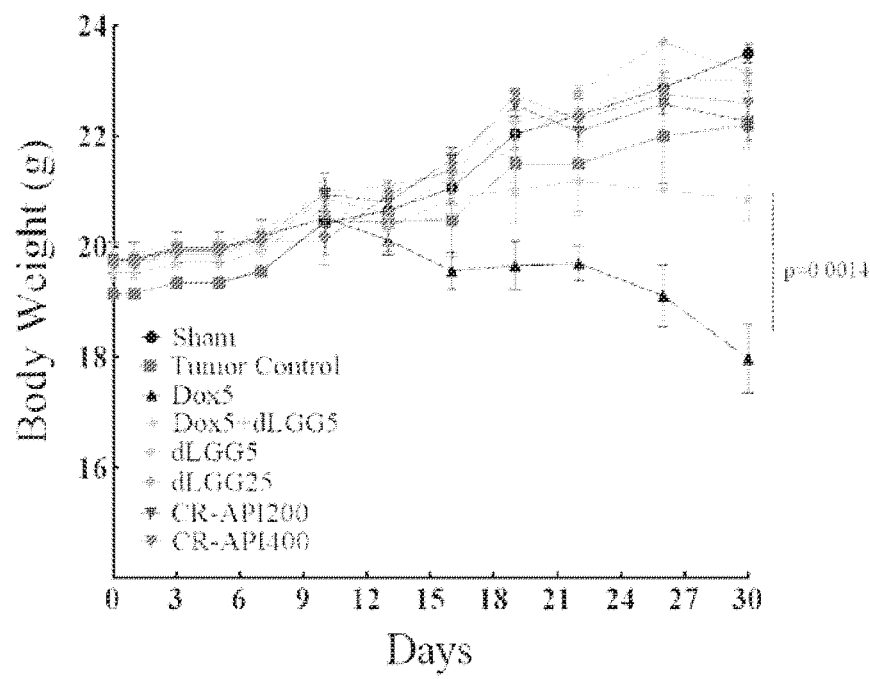

Combination Treatment with Low Dose dLGG Attenuates Doxorubicin-Induced Weight Loss in Test Animals The body weights of all test animals were recorded every 3 days for the duration of the treatment period (FIG. 4B). At day 30, we observed that only the Dox5-treated group show a dramatic loss of weight (10% of starting body weights of the test animals) compared with all the treatment groups. This phenomenon was attenuated in the Dox5+dLGG5 treatment group (P=0.0014), suggesting that dLGG alleviates the weight loss associated with doxorubicin treatment. No significant weight loss was observed for groups treated with either CR-API or dLGG only.

dLGG and CR-API Reduce TNBC Tumor Mass in a Dose-Dependent Manner

Figure 5A:
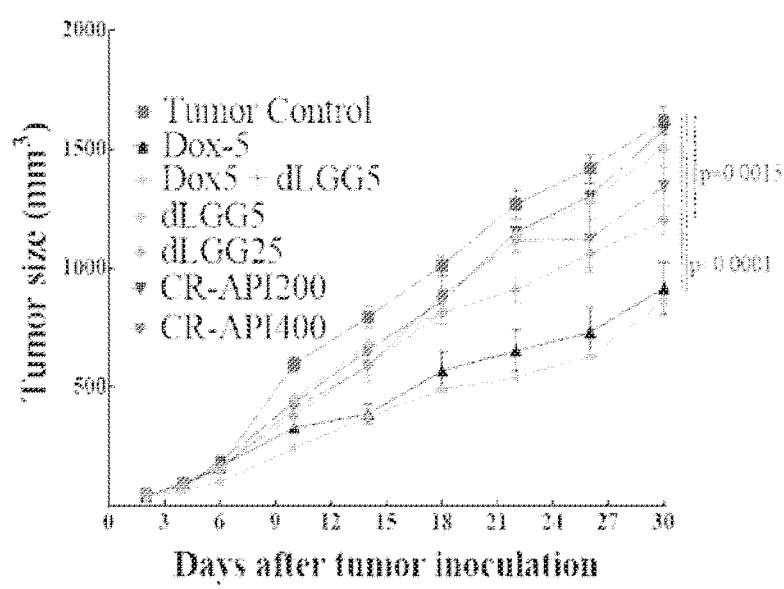
FIGS. 5A to 5C shows that CR-API and dLGG dose-dependently inhibited 4T1 tumor growth in mice.
Figure 5B:
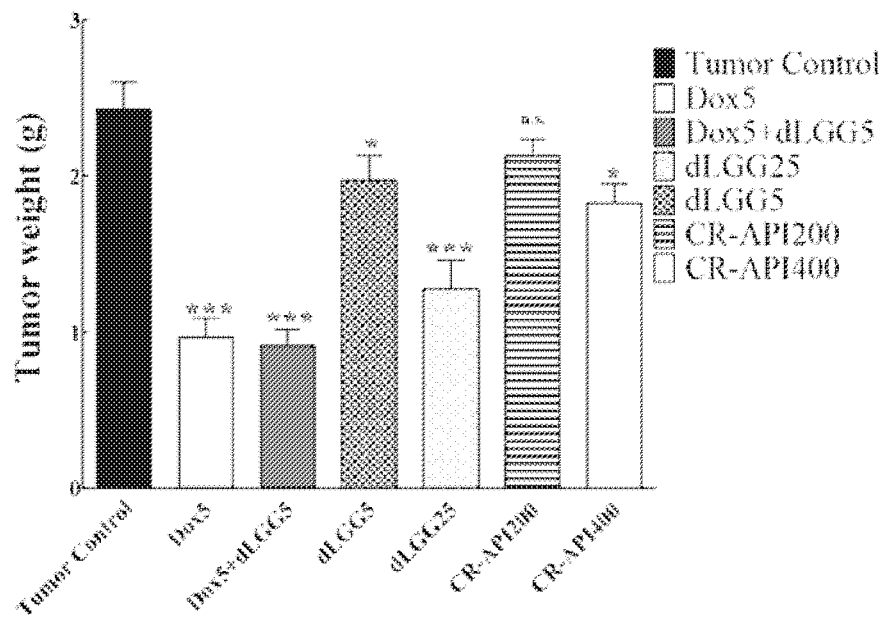
Figure 5C:
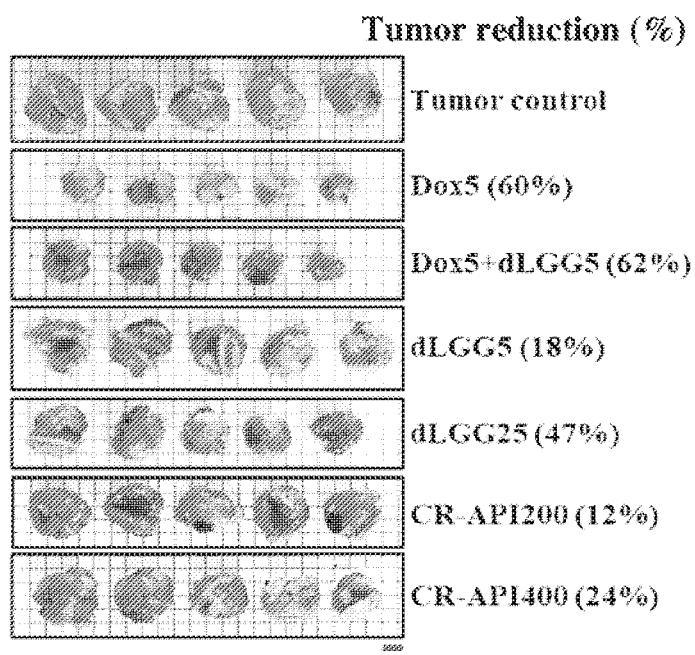

Tumor burden of all groups along with the experimental period were monitored (FIG. 5A). The measured tumor volume are highly statistically different between the tumor control group and Dox5 (P<0.0001), Dox5+dLGG5 (P=0.0015), or dLGG25 (P=0.0015) treated mice. The tumor weight of all treatment groups were also measured and compared with that of the tumor control group at endpoint (FIGS. 5B and 5C). dLGG treatment significantly and dose-dependently reduced tumor volumes by 18% (dLGG5) and 47% (dLGG25) (P<0.05) compared with the tumor control group. A 60% and 62% reduction (P<0.05) in tumor weight were observed for test animals treated with Dox5 and Dox5+dLGG5, respectively. The tumor weight was observed to be reduced by 12% (P=0.1526) and 24% (P=0.0528) by CR-API200 and CR-API400 treatment, respectively. Taken together, these results suggest that dLGG attenuate TNBC tumor growth in a dose dependent manner.

Figure 6A:
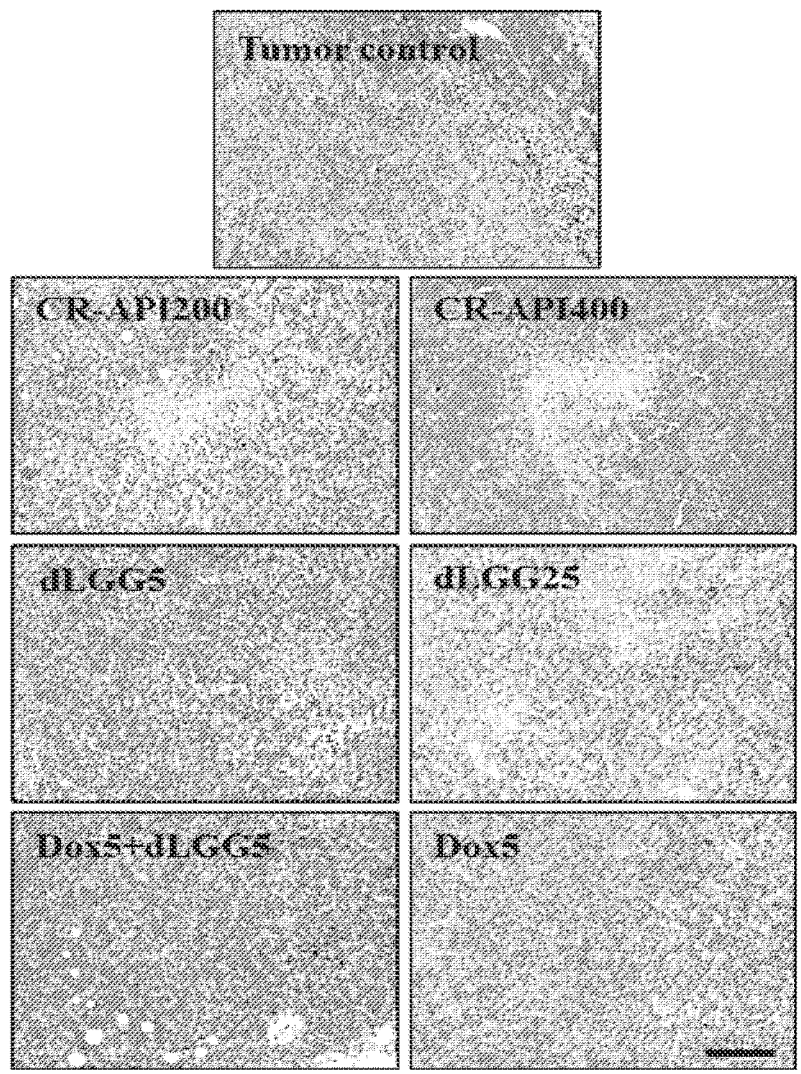
FIGS. 6A and 6B show that CR-API and dLGG treatment reduce tumor cell proliferation while inducing apoptosis. Representative IHC images of tumor tissues stained with (FIG. 6A) Ki67 (brownish color), a proliferation marker, and (FIG. 6B) cleave caspase 3, an apoptosis marker, with co-staining of nuclear indicator hematoxylin (bluish color) are shown (scale bar, 50 µm).

CR-API and dLGG Treatment Decrease Ki-67 Expression and Increase Caspase-3 Expression in Tumor Tissues IHC staining was performed to demonstrate the effects of CR-API or dLGG treatment of TNBC tumor tissues. We used Ki67, a cell proliferation marker, to see whether our extracts have a direct effect on tumor cell proliferation (FIG. 6A). Overexpression of Ki-67 in the tumor control group was observed, indicative of rapidly growing and proliferating cells. This phenomena was attenuated by treatment with CR-API or dLGG, regardless of dose used. A similar pattern was observed for Dox5 and Dox5+dLGG5 treated animals. These results suggest that dLGG inhibit tumor cell proliferation and might be effective to arrest tumor growth in TNBC.

Figure 6B:
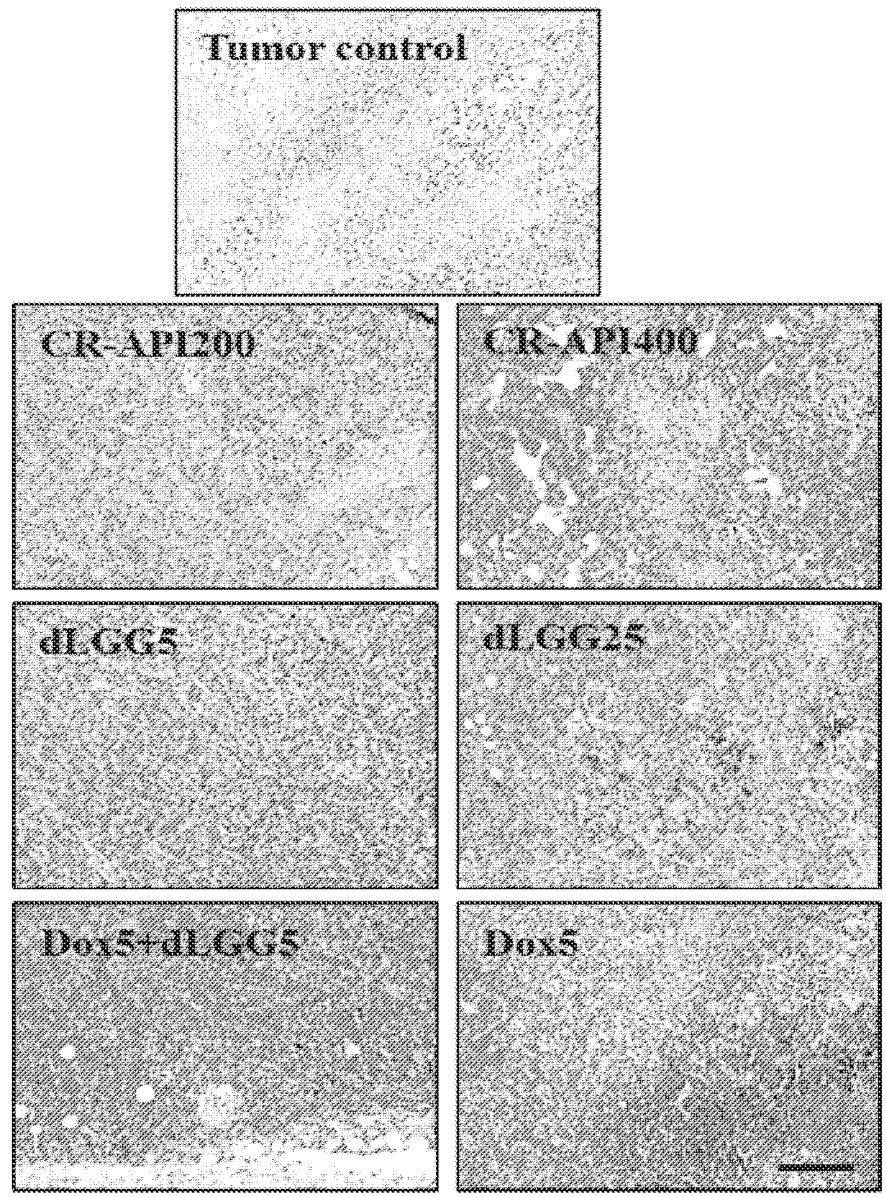

We also used cleaved caspase-3, an apoptosis marker, to determine the effect of compound treatment on cell apoptosis in tumor tissues (FIG. 6B). All treatment groups showed increased expression of cleaved caspase-3 compared with the vehicle control. Notably, Dox5, CR-API400 and dLGG25 treatments show higher caspase-3 expression compared with the low dose treatments and the Dox5+dLGG5 combination treatments. These results show that CR-API or dLGG treatment induce apoptosis in TNBC tumors, comparable to the apoptotic effects of doxorubicin treatment. These results are important the bioefficacy of either CR-API or dLGG as an inhibitor of tumor growth.

CR-API and dLGG Treatments Inhibit Distal Metastasis to the Lungs and Liver

Figure 7A:
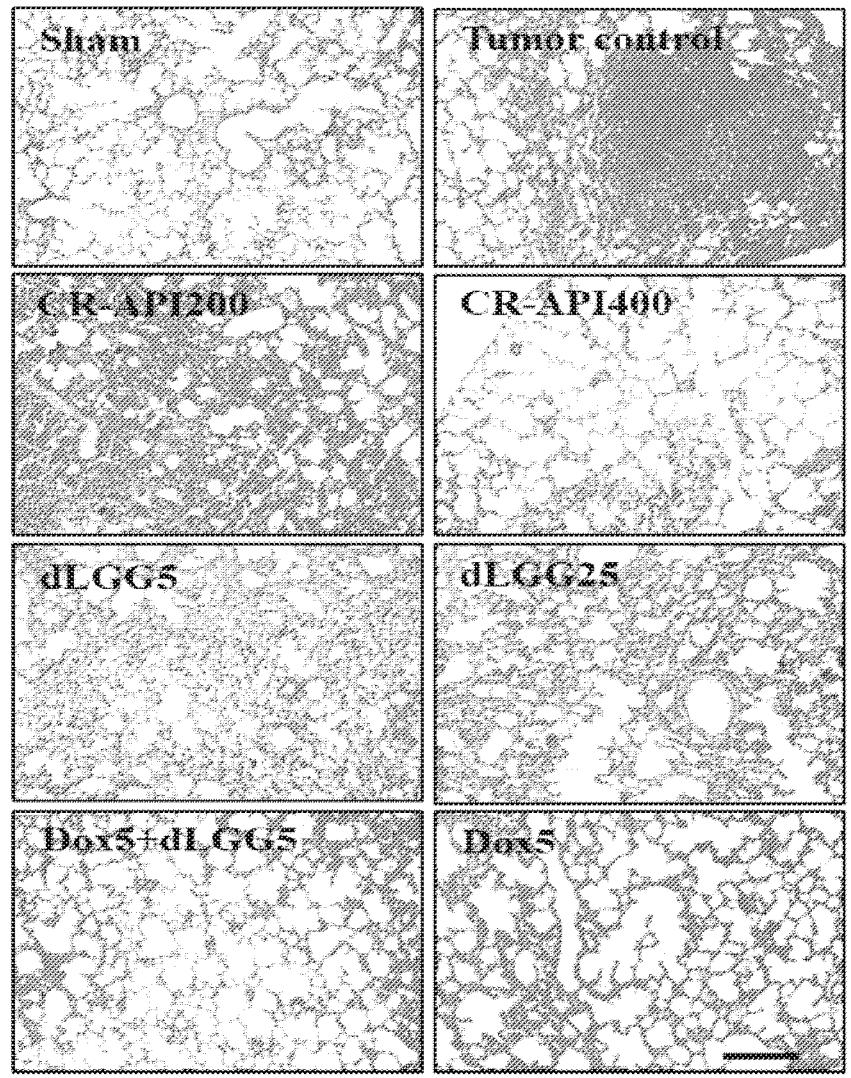
FIGS. 7A and 7B show that CR-API and dLGG treatments decrease TNBC metastasis to distal lung organ in mice.
Figure 7B:
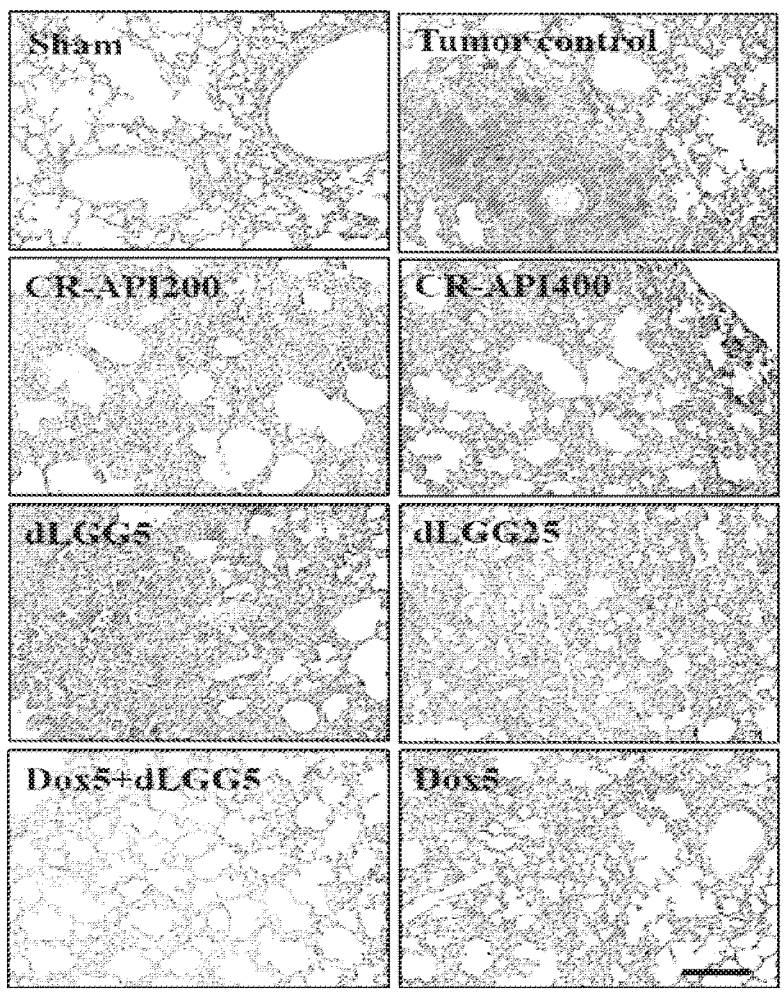
Figure 8A:
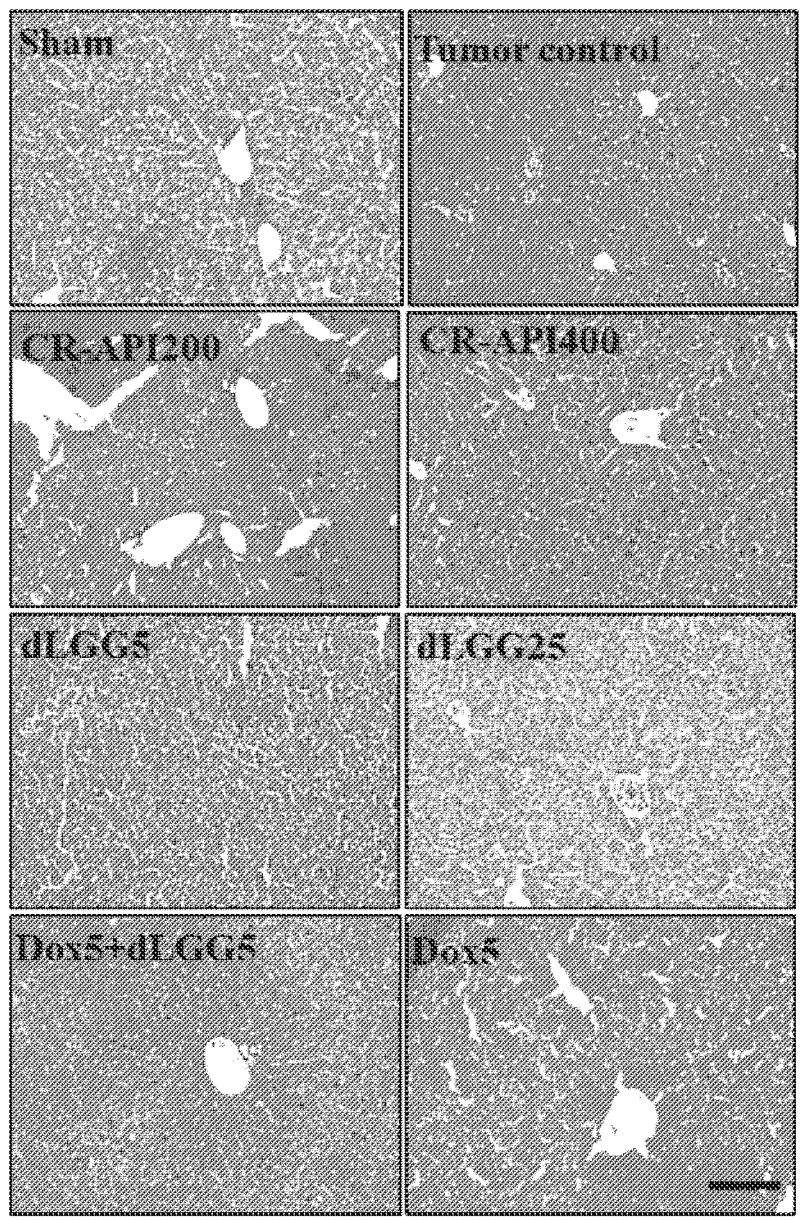
FIGS. 8A and 8B show that CR-API and dLGG treatments decrease TNBC metastasis to distal liver organ in mice. Representative H&E images (FIG. 8A) and IHC analysis (FIG. 8B) of Ki67-overexpressing cells in the of liver tissues suggest the presence of metastatic tumor nodules in the liver of the tumor control group, which were much reduced in compound- or extract treatment groups. Red arrows highlight the representative Ki67-overexpressing nodules in the images (scale bar, 50 µm).
Figure 8B:
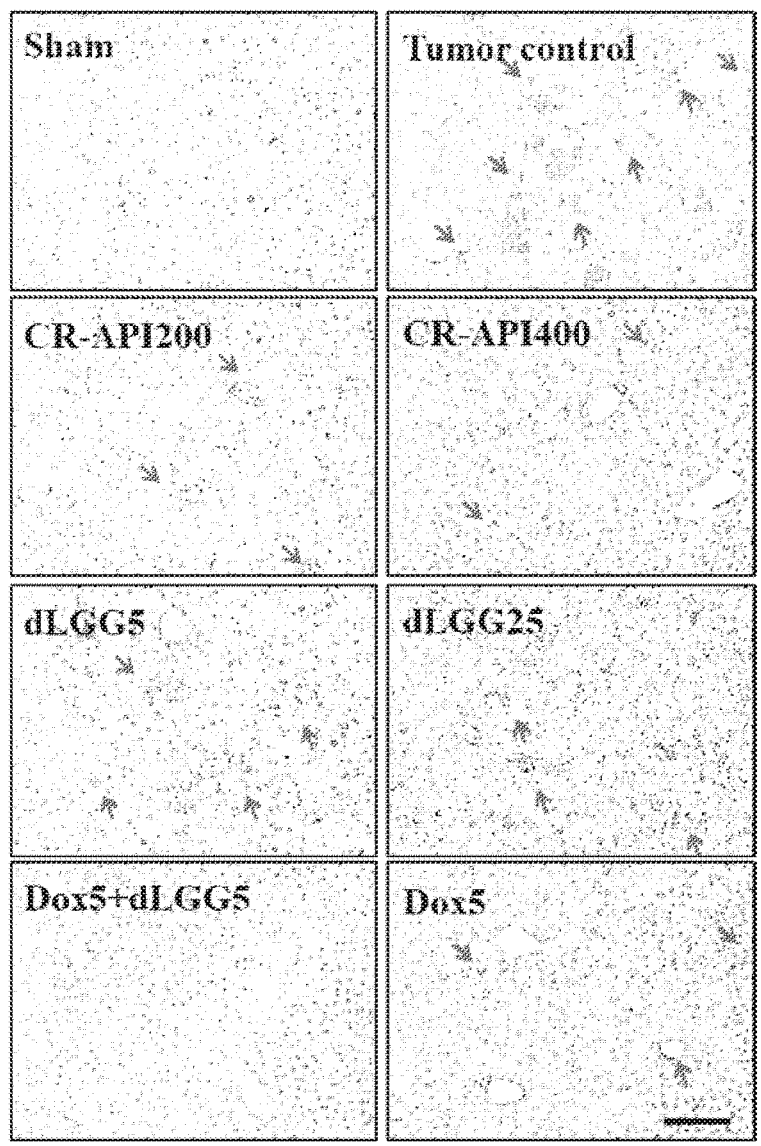

We observed spontaneous lung and liver metastasis, through the presence of visible tumor nodules, in the tumor control group. We therefore used H&E and IHC staining of Ki-67 in both organs to determine the presence of highly proliferating or micrometastatic cancer cells in these distal metastasis sites of the tumor control and compound-treated mice. As seen in FIGS. 7 and 8, tumor metastasis nodules in the lung and liver tissues of mice treated with Dox5, Dox5+dLGG5, dLGG5 and dLGG25, or CR-API200 and CR-API400 were less compared with the tumor control group. These results indicate that treatment with dLGG or CR-API inhibits TNBC tumor metastasis and is comparable to the effect of doxorubicin.

Figure 9A:
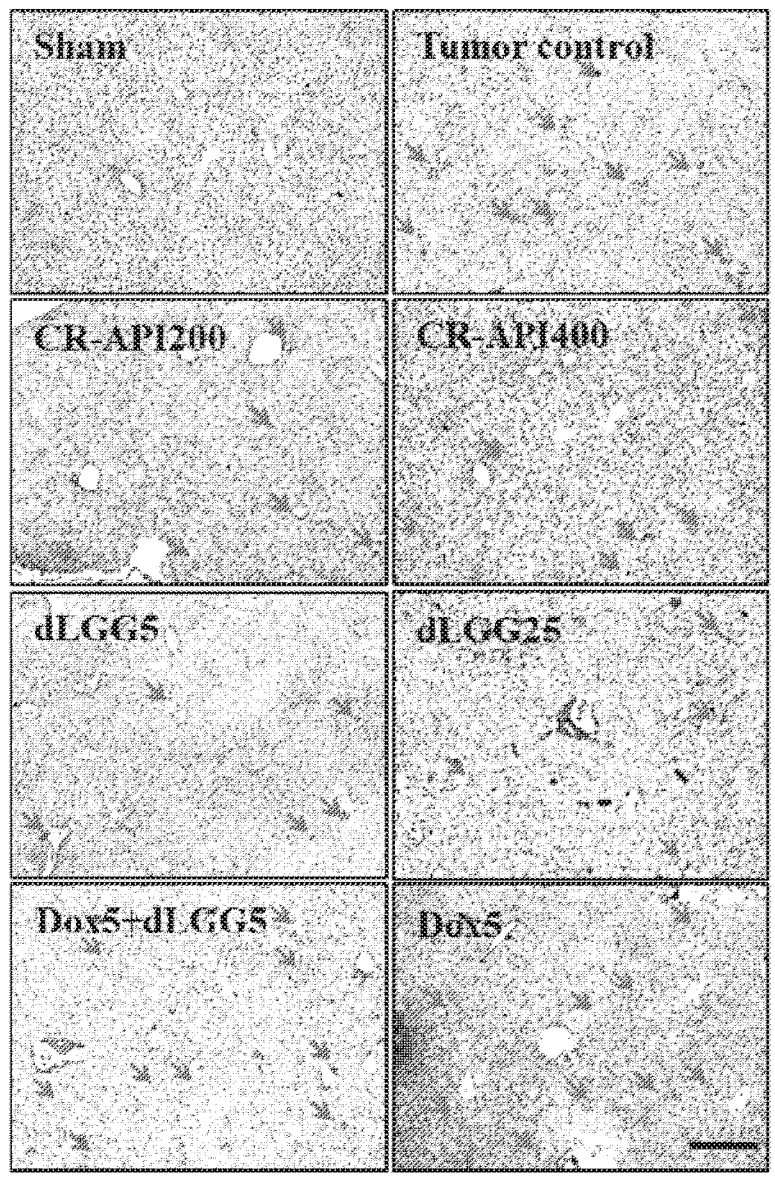
FIGS. 9A and 9B show that CR-API and dLGG treatment attenuate tumor- or doxorubicin-induced lung and liver inflammation. Representative IHC images of (FIG. 9A) liver and (FIG. 9B) lung tissues of all groups stained with pro-inflammatory COX-2 show that tumor- or Dox-induced inflammation in TNBC-metastasis organ sites were attenuated by dLGG or CR-API treatments (scale bar, 50 µm).
Figure 9B:
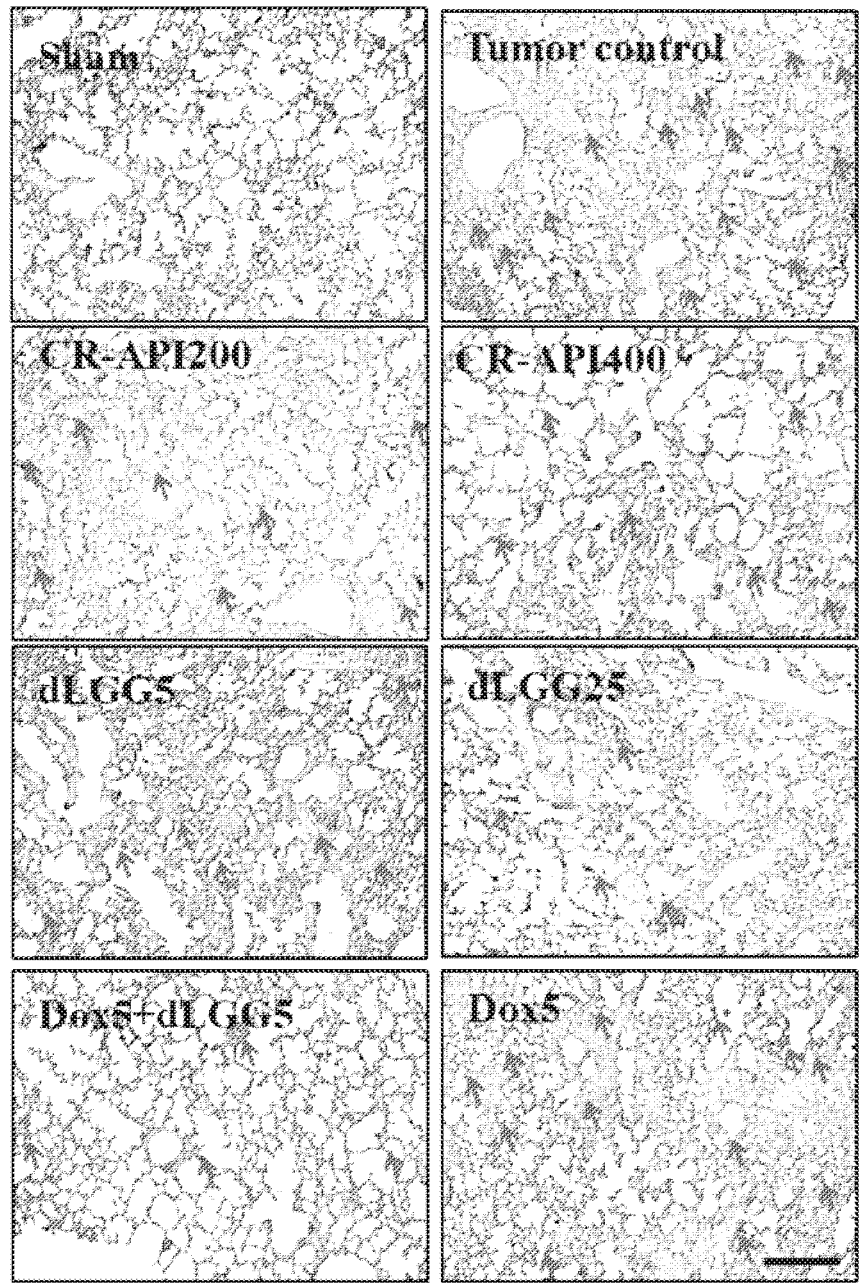

CR-API and dLGG Treatments Inhibit Tumor- or Doxorubicin-Induced Lung and Liver Inflammation An overall increase in pro-inflammatory COX-2 expression in the tumor tissues and in liver and lung organs indicates heightened inflammation, which may exacerbate tumor growth and metastasis or as indicators of other potential side effects (Minn J A, Gupta G P, Siegel P M, et al. (2005) Genes that mediate breast cancer metastasis to lung. Nature 436 (7050): 518-524; Chiang A C and Massague J. (2014) Molecular basis of metastasis. N Engl J Med 359 (26): 2814-2823). We measured and compared the COX-2 overexpression in the liver (FIG. 9A) and lung (FIG. 9B) tissues of the test animals. COX-2 expression in the organs of the dLGG or CR-API treated animals were decreased in a dose-dependent manner, comparable to the sham control group. Dox5 treatment, on the other hand, was observed to further induce COX-2 expression in these organs. Interestingly, in Dox5+dLGG5 combination treatment groups, COX-2 expression was decreased and is comparable to the expression level of dLGG5 or CR-API200 treatment alone. These results demonstrate that dLGG or CR-API treatment inhibits inflammation in organs that might be susceptible to TNBC metastasis. Moreover, these results suggest that dLGG treatment decrease systemic/multi-organ inflammation associated with doxorubicin treatment.

Figure 10:
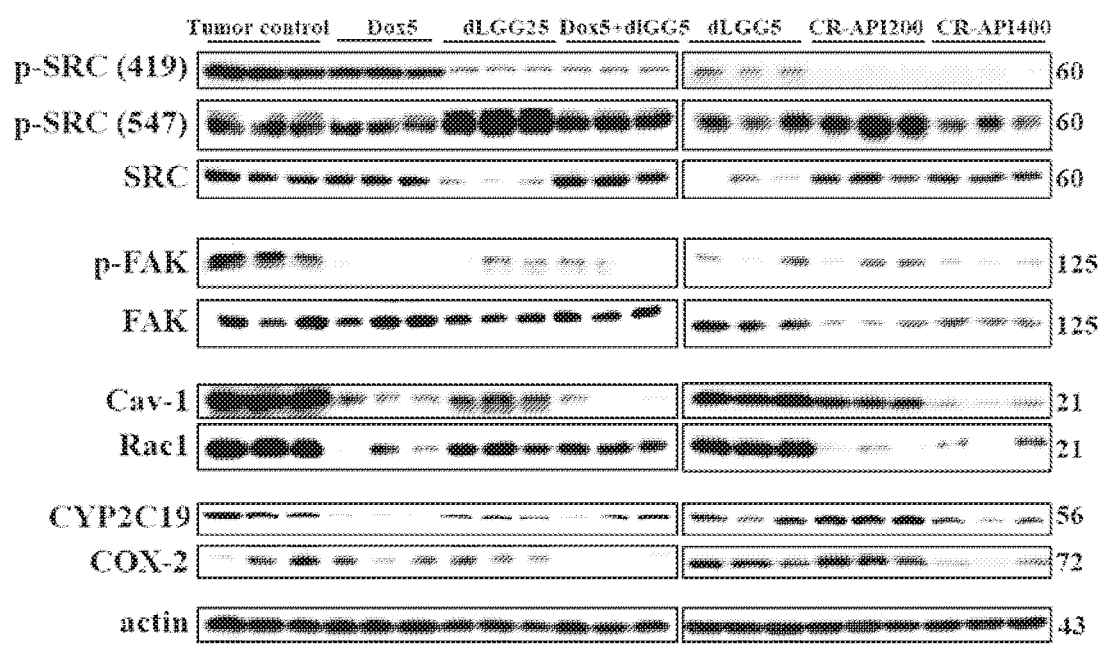
FIG. 10 shows that CR-API and dLGG treatment deregulate metastasis related signaling in tumor tissues. Western blot analysis shows that treatment with either CR-API or dLGG attenuates Src/FAK signaling cascade and influence the expression levels of membrane remodelling and lipid metabolism-related proteins.

CR-API and dLGG Attenuate the Expression of Metastasis-Related Proteins in TNBC Tumors We used western blot analysis to investigate the possible mechanism supporting how dLGG or dLGG-enriched extracts attenuated TNBC metastasis in the tumor tissues (FIG. 10). CYP2C19 and COX-2 were analyzed to serve as inflammatory markers and markers of bioactive lipid metabolism in the tumors (Panigrahy D, Kaipainen A, Greene E R, Huang S. (2015) Cytochrome P450-derived eicosanoids: the neglected pathway in cancer. Cancer Metastasis Reviews 29 (4):723-735). A dose dependent effect on attenuating the expression levels of both proteins were observed for all the dLGG and CR-API treatment groups. Combination treatment Dox5+dLGG5 also decreased the levels of these proteins compared with the group treated with Dox5 alone. These results show that dLGG may inhibit the pro-inflammatory tumor landscape influenced by metabolites derived from CYP19 or COX-2 in the tumor tissues contributing to its anti-proliferative and anti-metastatic effects. Moreover, the expression levels of membrane remodeling and microenvironment sensing proteins were also examined. Expression levels of Cav-1 and Rac1, two important players in cell motility and vesicle formation (Diaz J, Mendoza P, Silva P, Quest A F, Torres V A. (2014) A novel caveolin-1/p85α/Rab5/Tiam1/Rac1 signaling axis in tumor cell migration and invasion. Commun Integr Biol 7 (5):e972850), were decreased significantly in high dose treatment of dLGG, Dox5 and Dox5+dLGG5. Furthermore, activation of Src (p-Src$^{419}$) was significantly inhibited by all dlGG and CR-API treatments and in Dox5+dLGG5 group compared with the tumor control; much less or no effect at all was detected in the Dox5-treated group. Phosphorylation of FAK was significantly inhibited by high dose treatment of dLGG, CR-API, Dox5 and Dox5+dLGG5. Taken together, these results imply that dLGG and CR-API attenuate tumor metastasis by inhibiting the pro-inflammatory tumor microenvironment, membrane remodeling and tumor microenvironment sensing.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

That is claimed is:

1. A method of treatment for increasing a probability of survival of breast cancer and/or breast cancer metastasis in a subject in need of such treatment comprising administering to said subject an effective amount of *Crassocephalum rabens* extract or a compound represented by Formula I or a pharmaceutically acceptable derivative thereof;

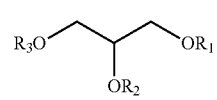

Formula I wherein $R_1$ and $R_2$, independently, is $C(O)R_a$ in which $R_a$ is $C_{15-17}$ alkyl having 0 to 3 double bonds, and $R_3$ is monogalactosyl or digalactosyl, and optionally a pharmaceutically acceptable carrier or excipient, wherein the treatment increases a probability of survival of the subject to metastasis of the breast cancer to the subject's lung, liver or brain.

2. The method according to claim 1, wherein the *Crassocephalum rabens* extract is an alcohol extract.

3. The method according to claim 2, wherein the alcohol is C1 to C4 alcohol.

4. The method according to claim 1, wherein the compound represented by Formula I is selected from the group consisting of 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1) and 1,2-di-O-α-linolenoyl-3-O-(6-O-α-galactopyranosyl-β-galactopyranosyl)-sn-glycerol (DGDG).

5. The method according to claim 1, wherein the breast cancer comprises breast cancer cells selected from the group consisting of ER+ breast cancer cells, Her2+ breast cancer cells and ER−, PR− and Her2− breast cancer cells.

6. The method according to claim 1, wherein the treatment comprising administration of the *Crassocephalum rabens* extract or compound represented by Formula I or pharmaceutically acceptable derivative thereof increases a probability of survival of the subject of the breast cancer as compared with a treatment consisting of administration of doxorubicin.

7. The method according to claim 1, which further comprises administering to *Crassocephalum rabens* extract or compound represent by Formula I or pharmaceutically acceptable derivative thereof to said subject with doxorubicin, epirubicin, bevacizumab, gemcitabine, 5-fluorouracil, capecitabine, cyclophosphamide, carboplatin, cisplatin, oxaliplatin, or vinblastine.

8. The method according to claim 7, wherein the administration of the *Crassocephalum rabens* extract or compound represented by Formula I or pharmaceutically acceptable derivative thereof attenuating side effects of the doxorubicin, epirubicin, bevacizumab, gemcitabine, 5-fluorouracil, capecitabine, cyclophosphamide, carboplatin, cisplatin, oxaliplatin, or vinblastine.

9. The method according to claim 8, wherein the side effects are selected from the group consisting of body weight loss, compromised immune response, cachexia, fatigue, cardiomyopathy, and COX-2 overexpression.

10. The method according to claim 8, wherein the *Crassocephalum rabens* extract is an alcohol extract.

11. The method according to claim 10, wherein the alcohol is C1 to C4 alcohol.

12. The method according to claim 8, wherein the compound represented by Formula I is selected from the group consisting of 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1) and 1,2-di-O-α-linolenoyl-3-O-(6-O-α-galactopyranosyl-β-galactopyranosyl)-sn-glycerol (DGDG).

13. The method according to claim 8, which comprises administering the doxorubicin, epirubicin, bevacizumab, gemcitabine, 5-fluorouracil, capecitabine, cyclophosphamide, carboplatin, cisplatin, oxaliplatin, or vinblastine to the subject together with the effective amount of *Crassocephalum rabens* extract, the compound represented by Formula I or the pharmaceutically acceptable derivative thereof.

* * * * *